United States Patent [19]
Takemoto et al.

[11] Patent Number: 4,780,528
[45] Date of Patent: Oct. 25, 1988

[54] TRIPEPTIDES AND SWEETENING AGENTS CONTAINING THE SAME
[75] Inventors: Tadashi Takemoto; Toyoto Hijiya; Toshihide Yukawa, all of Kawasaki, Japan
[73] Assignee: Ajinomoto Co., Inc., Tokyo, Japan
[21] Appl. No.: 794,788
[22] Filed: Nov. 4, 1985
[30] Foreign Application Priority Data Dec. 22, 1984 [JP] Japan ................. 59-271478

[51] Int. Cl.$^4$ ........................... C07C 103/52
[52] U.S. Cl. ................... 530/331; 530/801
[58] Field of Search ............ 530/300, 331, 801
[56] References Cited

U.S. PATENT DOCUMENTS

| | | | |
|---|---|---|---|
| 3,879,372 | 4/1975 | Boesten | 560/40 |
| 4,017,472 | 4/1977 | Farkas et al. | 560/40 |
| 4,127,534 | 11/1978 | Coy et al. | 525/54.11 |
| 4,428,938 | 1/1984 | Kisfaludy et al. | 530/330 |
| 4,491,541 | 1/1985 | de Castiglione et al. | 530/330 |
| 4,619,916 | 10/1986 | Di Stazio et al. | 530/331 |

FOREIGN PATENT DOCUMENTS

| | | | |
|---|---|---|---|
| 0787917 | 10/1962 | Canada | 530/331 |
| A1692768 | 4/1973 | Fed. Rep. of Germany. | |
| 1042488 | 9/1966 | United Kingdom | 530/331 |

OTHER PUBLICATIONS

Ariyoshi, "The Structure-Taste Relationships of Aspartyl Dipeptide Esters", *Agr. Biol. Chem.* 40, (5), 983-992, 1976.

Sukehiro et al, "Studies on Structure-Taste Relationships of Aspartyl Peptide Sweeteners. I. Syntheses and Properties of L-Aspartyl-D-Alanine Amides", *Science of Human Life*, vol. 11, Nos. 1-2, Mar. 1977.

Chemical Abstracts, vol. 87, No. 21, Nov. 21, 1977, p. 614, Abstract No. 168407h, Columbus, Ohio, US; M. Sukehiro et al. "Structure-Taste Relations of Aspartyl Peptide Sweeteners. I. Syntheses and Properties..." & Seikatsu Kagaku 1977.

*Primary Examiner*—John Kight
*Assistant Examiner*—Nathan M. Nutter
*Attorney, Agent, or Firm*—Oblon, Fisher, Spivak, McClelland & Maier

[57] ABSTRACT

Tripeptide sweeteners represented by formula (I)

$$X-Asp-Y-OR$$

wherein
X is glycine or a D or DL-isomer of alanine, α-aminobutyric acid, serine, threonine, norvaline, asparagine, B-methyl aspartate, proline or pipecolic acid, and
Y is a D, L or DL-isomer of alanine, phenylalanine, phenylglycine, serine or β-aminobutyric acid or a salt thereof, and
R is methyl, ethyl, propyl or isopropyl, are disclosed.

6 Claims, No Drawings

TRIPEPTIDES AND SWEETENING AGENTS CONTAINING THE SAME

DETAILED DESCRIPTION OF THE INVENTION

This invention relates to new tripeptides, salts thereof, and sweetening agents containing the same as effective ingredient.

Supply of foods has become abundant in recent years in both quantity and quality. As a result, obesity caused by excessive intake of sugars, and various diseases derived therefrom, are now an issue of social concern. Under the circumstances, development of low-calorie or no-calorie sweeteners is hoped for as a substitute for sucrose.

The object of this invention is to provide new tripeptides and their salts free from toxicity problem and showing soft sweetness, and to provide low-calorie sweetening agents containing said tripeptide or its salt.

The compounds of this invention are represented by the following general formula (I)

$$X-Asp-Y-OR \qquad (I)$$

wherein X is an amino acid residue linked, at its carboxyl group, to the amino group of L-aspartic acid through peptide bonding (e.g., the residue of glycine, alanine, α-aminobutyric acid, serine, threonine, norvaline, asparagine, β-methyl aspartate, proline, α-aminoisobutyric acid, pipecolic acid, azetidine-carboxylic acid and aziridine-carboxylic acid); Asp denotes an L-aspartic acid residue which is linked, at its amino group, to the amino acid residue X through peptide bonding and is connected, at its carboxyl group attached to the amino-substituted carbon atom, to the amino acid residue Y through peptide bonding; Y stands for an amino acid residue which is linked, at its amino group, to Asp through peptide bonding and connected, at its carboxyl group, to an alcohol through ester bonding (e.g., the residue of glycine, alanine, phenylalanine, phenylglycine, valine, tyrosine, serine, threonine, α-aminobutyric acid, α-aminoisobutyric acid, norvaline, aminomalonic acid, methionine, L-aspartic acid, glutamic acid, norleucine and other amino acids); OR expresses an alcohol residue linked, at its hydroxyl group, to the amino acid residue Y through ester bonding; R denotes an alkyl such as methyl, ethyl, propyl, isopropyl, butyl and isobutyl, or a cyclic alkyl such as cyclohexyl; the amino acid residue X represents D-or DL-isomer except when it is glycine or α-aminoisobutyric acid; and the amino acid residue Y represents L-, D- or DL-isomer when it is not an amino acid having no center of optical activity like glycine.

Thus the compounds of this invention are tripeptides derived from an amino acid corresponding to the residue X, L-aspartic acid, and an amino acid ester corresponding to the residue Y.

As examples of the salts of the compounds of this invention there may be mentioned inorganic acid salts such as hydrochlorides, sulfates and phosphates, organic acid salts such as acetates, formates, propionates, sulfamates, ascorbates, cinnamates, oxalates, citrates, tartrates, lactates, malonates, maleates and succinates, salts with alkali metals such as sodium and potassium salts, salts with alkali earth metals such as calcium and magnesium salts, and amine salts such as monoethanolamine salts.

The compounds of this invention can be easily prepared by known techniques commonly used for peptide synthsis. For example, β-benzyl N-benzyloxycarbonyl-L-aspartate [hereinafter abbreviated as Z-Asp(OBzl)] is condensed with an amino acid ester correponding to the residue Y in the presence of a condensation agent, such as dicyclohexyl carbodiimide (hereinafter abbreviated as DCC), followed by removal of the protective group, giving an α-L-aspartyl amino acid ester. This dipeptide ester is then allowed to react with an active ester of N-protected amino acid that corresponds to the residue X (for example, N-hydroxysuccinimide ester or p-nitrophenyl ester) in a mixture of water and an organic solvent, such as dioxane, tetrahydrofuran and dimethylformamide, giving an N-protected compound of this invention. The corresponding compound of this invention and a salt thereof can be obtained by removal of the protective group.

For the synthesis of compounds in which Y is phenylalanine residue and R is methyl, it is advantageous to react α-L-aspartyl-L-phenylalanine methyl ester (obtainable by the method described in U.S. Pat. No. 3,786,039) with an active ester of N-protected amino acid residue X to form N-protected compound of this invention, followed by removal of the protective group. Benzyloxycarbonyl, t-butoxycarbonyl or formyl is used as the protective group. Removal of these protective groups may be effected by known methods.

The compounds of this invention are obtained in the form of free amino acid or as a salt. These can be converted from one form to the other by known methods.

The compounds of this invention can be isolated and purified by commonly used techniques, such as recrystallization from a suitable solvent, reprecipitation, chromatography and other methods. The compounds thus isolated and purified can be identified by NMR, mass spectrometry, TLC and other analytical techniques.

Organoleptic tests (comparison with sucrose at threshold values—0.6 g/dl solution for sucrose) revealed that the compounds of this invention show soft sweetness, with D-alanyl-α-L-aspartyl-L-phenylalanine methyl ester being the best in terms of quality and intensity of sweetness. Its degree of sweetness was 180 times as high as that of sucrose. The sweetness degree of D-prolyl-α-L-aspartyl-L-phenylalanine methyl ester and D-alanyl-α-L-aspartyl-D-alanine isopropyl ester were both 50 times as high.

The present tripeptide sweetening agents are water soluble, stable substances which can be utilized in a variety of physical forms, e.g. as powders, tablets, syrups, etc. Liquid or solid carriers such as water, glycerol, starch, sorbitol, salt, citric acid and other suitable non-toxic substances can be utilized also. These compositions are particularly valuable as sweetening agents for edible materials. Examples of such materials are fruits, vegetables, juices, meat products such as ham or bacon, sweetened milk products, egg products, salad dressings, ice creams and sherbets, icings, syrups, cake mixes and beverages such as carbonated soft drinks and wines.

The compounds and their salts of this invention may be used in combination with other types of sweeteners unless any special inconvenience exists.

This invention will become more apparent from the following examples.

EXAMPLE 1

D-Alanyl-α-L-aspartyl-L-phenylalanine methyl ester (A) N-Benzyloxycarbonyl-D-alanine N-hydroxysuccinimide ester In 50 ml of tetrahydrofuran were dissolved 4.5 g of N-benzyloxycarbonyl-D-alanine and 2.3 g of N-hydroxysuccinimide. A solution of 4.1 g of dicyclohexylcarbodiimide in 10 ml of tetrahydrofuren was added oo the solution under ice cooling. The mixture was stirred for 1 hour under ice cooling and then at room temperature overnight. Precipitated dicyclohexylurea was separated by filtration. The filtrate was concentrated under reduced pressure and the residue was recrystallized from ethanol. Yield 4.5 g.

(B) N-Benzyloxycarbonyl-D-alanyl-α-L-aspartyl-L-phenylalanine methyl ester

In 50 ml of water were dissolved 2.4 g of α-L-aspartyl-L-phenylalanine methyl ester and 0.7 g of sodium bicarbonate. A solution of 1.9 g of N-benzyloxycarbonyl-D-alanine N-hydroxysuccinimide ester in 50 ml of dioxane was added to the solution. The mixture was stirred at room temperature for 5 hours. After the pH was adjusted to 2.5 with 6N hydrochloric acid, 150 ml of ethyl acetate was added to the mixture. The separated ethyl acetate layer was wahsed with water and a saturated sodium chloride aqueous solution and dried over anhydrous sodium sulfate. Sodium sulfated was removed, and ethyl acetate was distilled off under reduced pressure. The residue was reprecipitated from ethyl acetate/hexane. Yield 2.1 g.

(C) D-Alanyl-α-L-aspartyl-L-phenylalanine methyl ester

In a solvent mixture of 75 ml of methanol and 75 ml of water was dissolved 2.1 g of N-benzyloxycarbonyl-D-alanyl-α-L-aspartyl-L-phenylalanine methyl ester, followed by reduction at room temperature for 4 hours in a hydrogen flow using palladium-carbon as a catalyst. The catalyst was filtered off and the filtrate was concentrated under reduced pressure. The residue was recrystallized from water-acetone. Yield, 1.3 g; m.p., 228°–230° C.

EXAMPLE 2

D-Alanyl-α-L-aspartyl-L-phenylalanine methyl ester hydrochloride (A) N-t-Butoxycarbonyl-D-alanine N-hydroxysuccinimide ester In 60 ml of tetrahydrofuran were dissolved 5 g of N-t-butoxycarbonyl-D-alanine and 3.2 g of N-hydroxysuccinimide. A solution of 5.8 g of dicyclohexylcarbodiimide in 15 ml of tetrahydrofuren was added to the solution under ice cooling. The mixture was stirred for 1 hour under ice cooling and then at room temperature overnight. Precipitated dicyclohexylurea was separated by filtration. The filtrate was concentrated under reduced pressure and the residue was recrystallized from ethanol. Yield 5.3 g.

(B) N-t-Butoxycarbonyl-D-alanyl-αL-aspartyl-L-phenylalanine methyl ester

In 45 ml of water were dissolved 2.2 g of α-L-aspartyl-L-phenylalanine methyl ester and 0.6 g of sodium bicarbonate. A solution of 1.7 g of N-t-butoxycarbonyl-D-alanine N-hydroxysuccinimide ester in 45 ml of dioxane was added to the solution. The mixture was stirred at room temperature for 5 hours. After the pH was adjusted to 2.5 with 6N hydrochloric acid, 150 ml of ethyl acetate was added to the mixture. The separated ethyl acetate layer was washed with water and a saturated sodium chloride aqueous solution and then dried over anhydrous Glauber's salt. Glauber's salt was removed, and ethyl acetate was distilled off under reduced pressure. The residue was reprecipitated from ethyl acetate/hexane. Yield 2.0 g.

(C) D-Alanyl-α-L-aspartyl-L-phenylalanine methyl ester hydrochloride

To 20 ml of 4N-HCl/dioxane was added 2.0 g of N-t-butoxycarbonyl-D-alanyl-α-L-aspartyl-L-phenylalanine methyl ester under ice cooling. The mixture was stirred for 1 hour. To the reaction mixture was added 150 ml of ethyl ether. Precipitated crystals were collected by filtration. Yield, 1.6 g; m.p., 205°–208° C. (decomposed).

EXAMPLE 3

D-Seryl-α-L-aspartyl-L-phenylalanine methyl ester (A) D-Seryl-α-L-aspartyl-L-phenylalanine methyl ester hydrochloride In a manner similar to Example 2 (B) and (C), 2.3 g of D-seryl-α-L-aspartyl-L-phenylalanine methyl ester was obtained from 2.4 g of N-t-butoxycarbonyl-D-serine N-hydroxy succinimide ester prepared in a manner similar to Example 2 (A) and 3.0 g of α-L-aspartyl-L-phenylalanine methyl ester.

(B) D-Seryl-α-L-aspartyl-L-phenylalanine methyl ester

In 50ml of water was dissolved 1.1 g of D-seryl-α-L-aspartyl-L-phenylalanine methyl ester hydrochloride. After the solution was neutralized with sodium bicarbonate, the solution was adsorbed on a column (50 ml) of styrene divinyl type adsorption resin (manufactured by Mitsubishi Chemical Industries, Ltd. "Adsorption Resin SP-207"). After washing with 200 ml of water, elution was performed with 200 ml of water/methanol=50/50 vol%. The solvent was removed by distillation to obtain 0.8 g of white powders. m.p. 196°–199° C.

EXAMPLE 4

β-Methyl-α-D-aspartyl-α-L-aspartyl-L-phenylalanine methyl ester (A) β-Methyl-α-D-aspartyl-α-L-aspartyl-L-phenylalanine methyl ester hydrochloride In a manner similar to Example 2 (B) and (C), 2.0 g of β-methyl-α-D-aspartyl-α-L-aspartyl-L-phenylalanine methyl ester hydrochloride was obtained from 2.1 g of β-methyl-N-t-butoxycarbonyl-D-aspartic acid N-hydroxysuccinimide ester prepared in a manner similar to Example 2 (A) and 2.4 g of α-L-aspartyl-L-phenylalanine methyl ester.

(B)

β-Methyl-α-D-aspartyl-α-L-aspartyl-L-phenylalanine methyl ester

In a manner similar to Example 3 (B), 0.6 g of β-methyl-α-D-aspartyl-α-L-aspartyl-L-phenylalanine methyl ester was obtained from 1.0 g of the above-described hydrochloride. m.p. 172°–175° C.

EXAMPLE 5

DL-α-Aminobutyryl-α-L-aspartyl-L-phenylalanine methyl ester

In a manner similar to Example 1, 1.9 g of DL-α-aminobutyryl-α-L-aspartyl-L-phenylalanine methyl ester was obtained from 2.4 g of N-benzyloxycarbonyl-DL-α-aminobutyric acid and 2.4 g of α-L-aspartyl-L-phenylalanine methyl ester. m.p. 206°–208° C.

EXAMPLE 6

Glycyl-α-L-aspartyl-L-phenylalanine methyl ester

In a manner similar to Example 2 and Example 3 (B), 0.8 g of glycyl-α-L-aspartyl-L-phenylalanine methyl ester was obtained from 1.7 g of N-t-butoxycarbonyl-glycine and 2.4 g of α-L-aspartyl-L-phenylalanine methyl ester. m.p. 233°–235° C.

EXAMPLE 7

D-Norvalyl-α-L-aspartyl-L-phenylalanine methyl ester hydrochloride

In a manner similar to Example 2, 2.4 g of D-norvalyl-α-L-aspartyl-L-phenylalanine methyl ester hydrochloride was obtained from 2.3 g of N-t-butoxycarbonyl-D-norvaline and 2.4 g of α-L-aspartyl-L-phenylalanine methyl ester. m.p. 187°–190° C. (decomposed).

EXAMPLE 8

D-Threonyl-α-L-aspartyl-L-phenylalanine methyl ester

In a manner similar to Example 1, 1.4 g of D-threonyl-α-L-aspartyl-L-phenylalanine methyl ester was obtained from 2.5 g of N-benzyloxycarbonyl-D-threonine and 2.4 g of α-L-aspartyl-L-phenylalanine methyl ester. m.p. 195°–199° C.

EXAMPLE 9

DL-Alanyl-α-L-aspartyl-L-phenylalanine methyl ester

In a manner similar to Example 1, 1.6 g of DL-alanyl-α-L-aspartyl-L-phenylalanine methyl ester was obtained from 2.2 g of N-benzyloxycarbonyl-DL-alanine and 2.4 g of α-L-aspartyl-L-phenylalanine methyl ester. m.p. 206°–209° C.

EXAMPLE 10

D-Asparaginyl-α-L-aspartyl-L-phenylalanine methyl ester

In a manner similar to Example 1, 1.7 g of D-asparaginyl-α-L-aspartyl-L-phenylalanine methyl ester was obtained from 2.7 g of N-benzyloxycarbonyl-D-asparagine and 2.4 g of α-L-aspartyl-L-phenylalanine methyl ester. m.p. 203°–205° C.

EXAMPLE 11

D-Prolyl-α-L-aspartyl-L-phenylalanine methyl ester (A) α-L-aspartyl-L-phenylalanine methyl ester Triethylamine (1.4 ml) was added to a suspension of L-phenylalanine methyl ester hydrochloride (2.16 g) in 50 ml of chloroform. To the resulting solution was admixed Z-Asp(OBzl) (3.6 g), a solution of 2.06 g DCC in 10 ml chloroform was added under ice cooling, and the mixture was stirred under ice cooling for one hour and then at room temperature overnight.

Precipitated dicyclohexylurea was filtered off, the filtrate was concentrated under reduced pressure, and the residue was dissolved in 150 ml of ethyl acetate. This solution was washed with 2N-HCl, water, 4% aqueous solution of sodium bicarbonate, water and saturated aqueous solution of sodium chloride in that order, and dried over anhydrous sodium sulfate. After filtering off the drying agent, the filtrate was concentrated under reduced pressure.

The residue was dissolved in 100 ml of 80% aqueous acetic acid, and the solution was subjected to catalytic reduction under a hydrogen gas stream at room temperature for four hours using palladium-carbon as catalyst. After filtering off the catalyst, the filtrate was concentrated under reduced pressure, and the residue was recrystallized from water, giving 1.9 g of α-L-aspartyl-L-phenylalanine methyl ester.

(B) N-Benzyloxycarbonyl-D-proline N-hydroxysuccinimide ester

A solution of 10.3 g DCC in 30 ml tetrahydrofuran was added under ice cooling to a solution of 12.5 g N-benzyloxycarbonyl-D-proline and 5.8 g N-hydroxysuccinimide in 150 ml tetrahydrofuran. The mixture was stirred under ice cooling for one hour and then at room temperature overnight.

After precipitated dicyclohexylurea was filtered off, the filtrate was concentrated under reduced pressure, and the residue was recrystallized from ethanol, affording 12.1 g of N-benzyloxycarbonyl-D-proline N-hydroxysuccinimide ester.

(C)

N-Benzyloxycarbonyl-D-prolyl-α-L-aspartyl-L-phenylalanine methyl ester

To a solution of 1.9 g α-L-aspartyl-L-phenylalanine methyl ester and 0.6 g sodium bicarbonte in 50 ml water, was added with stirring a solution of 2.4 g N-benzyloxycarbonyl-D-proline N-hydroxysuccinimide ester in 50 ml dioxane, and stirring was continued at room temperature for five hours.

After the pH was adjusted to 2.5 with 6N-HCl, 150 ml ethyl acetate was added and the mixture was thoroughly agitated. The organic layer was collected, washed with water and then with saturated aqueous solution of sodium chloride, and dried over anhydrous sodium sulfate. After filtering off the drying agent, the filtrate was concentrated under reduced pressure, and the residue was purified by reprecipitation with ethyl acetate/hexane, giving 2.6 g of N-benzyloxycarbonyl-D-prolyl-α-L-aspartyl-L-phenylalanine methyl ester.

(D) D-Prolyl-α-L-aspartyl-L-phenylalanine methyl ester

N-Benzyloxycarbonyl-D-prolyl-α-L-aspartyl-L-phenylalanine methyl ester (2.6 g) was dissolved in 100 ml of 80% aqueous acetic acid, and the solution was subjected to catalytic reduction in a hydrogen gas stream at room temerature for four hours using palladium/carbon as catalyst. After filtering off the catalyst, the filtrate was concentrated to dryness under reduced pressure, affording 1.7 g of white powder. M.p.: 238°–241.5° C.

EXAMPLE 12

(A) N-t-Butoxycarbonyl-DL-2-piperidinecarboxylic acid N-hydroxysuccinimide ester A solution of 4.1 g DCC in 10 ml tetrahydrofuran was added under ice cooling to a solution of 4.6 g N-t-butoxycarbonyl-DL-2-piperidinecarboxylic acid and 2.3 g N-hydroxysuccinimide in 70 ml tetrahydrofuran. The mixture was stirred under ice cooling for one hour and then at room temperature overnight.

Precipitated dicyclohexylurea was filtered off, and the filtrate was concentrated under reduced pressure, giving 5.2 g of oil.

(B) N-t-Butoxycarbonyl-DL-2-piperidinecarbonyl-α-L-aspartyl-L-phenylalanine methyl ester To a solution of 1.9 g α-L-aspartyl-L-phenylalanine methyl ester and 0.6 g sodium bicarbonte in 50 ml water, was added with stirring a solution of 2.3 g oil (prepared in (A) above) in 50 ml dioxane, and stirring was continued at room temperature for five hours.

After the pH was adjusted to 2.5 with 6N-HCl, 150 ml ethyl acetate was added and the mixture was thoroughly agitated. The organic layer was collected, washed with water and then with saturated aqueous solution of sodium chloride, and dried over anhydrous sodium sulfate. After filtering off the drying agent, the filtrate was concentrated under reduced pressure, giving 2.6 g of oil.

(C) DL-2-Piperidinecarbonyl-α-L-aspartyl-L-phenylalanine methyl ester hydrochloride 4N-HCl/dioxane (20 ml) was added under ice cooling to 2.6 g of the oil obtained in (B) above, and the mixture was stirred at room temperature for one hour. Ethyl ether was added to the reaction mixture, and the crystals which separated out were collected by filtration. Yield: 2.1 g.

(D) DL-2-Piperidinecarbonyl-α-L-aspartyl-L-phenylalanine methyl ester

A solution of DL-2-piperidinecarbonyl-α-L-aspartyl-L-phenylalanine methyl ester hydrochloride (2.1 g) in 50 ml water was neutralized with sodium bicarbonate and passed through a column (50 ml) packed with an adsorption resin of styrene/divinylbenzene type (Mitsubishi Chemical Industries, Ltd., "Adsorption Resin SP-207"). After washing the column with 200 ml water, the adsorbed portion was eluted with 200 ml of water/methanol (50/50 by volume), and the solvents were removed by distillation, affording 1.7 g of white powder M.p.: 225°–227° C.

EXAMPLE 13

D-Prolyl-α-L-aspartyl-D-serine isopropyl ester (A) α-L-Aspartyl-D-serine isopropyl ester This compound was prepared from 1.8 g D-serine isopropyl ester hydrochloride and 3.6 g Z-Asp(OBzl) in a manner similar to Example 11 (A). Yield: 1.7 g.

(B) D-Prolyl-α-L-aspartyl-D-serine isopropyl ester

This compound was prepared from 1.7 g α-L-aspartyl-D-serine isopropyl ester and 2.4 g N-benzyloxycarbonyl-D-proline N-hydroxysuccinimide ester in a manner similar to Example 11 (C) and (D). Yield: 1.7 g, m.p.: 230°–233° C.

EXAMPLE 14

D-Prolyl-α-L-aspartyl-D-alanine propyl ester (A) α-L-Aspartyl-D-alanine propyl ester This compound was prepared from 1.7 g D-alanine propyl ester and 3.6 g Z-Asp(OBzl) in a manner similar to Example 11 (A). Yield: 1.6 g.

(B) D-Prolyl-α-L-aspartyl-D-alanine propyl ester

This compound was prepared from 1.6 g D-prolyl-α-L-aspartyl-D-alanine propyl ester and 2.4 g N-benzyloxycarbonyl-D-proline N-hydroxysuccinimide ester in a manner similar to Example 11 (C) and (D). Yield: 1.7 g, m.p.: 233°–235° C.

EXAMPLE 15

D-Prolyl-α-L-aspartyl-L-phenylglycine methyl ester (A) α-L-Aspartyl-L-phenylglycine methyl ester This compound was prepared from 2.0 g L-phenylglycine methyl ester hydrochloride and 3.6 g Z-Asp(OBzl) in a manner similar to Example 11 (A). Yield: 1.8 g.

(B) D-Prolyl-α-L-aspartyl-L-phenylglycine methyl ester

This compound was prepared from 1.8 g α-L-aspartyl-L-phenylglycine methyl ester and 2.4 g N-benzyloxycarbonyl-D-proline N-hydroxysuccinimide ester in a manner similar to Example 11 (C) and (D). Yield: 1.7 g, m.p.: 247°–249° C.

EXAMPLE 16

D-Alanyl-α-L-aspartyl-D-alanine isopropyl ester (A) α-L-Aspartyl-D-alanine isopropyl ester Triethylamine (1.4 ml) was added to a suspension of D-alanine isopropyl ester hydrochloride (1.7 g) in 50 ml of chloroform. To the resulting solution was admixed Z-Asp(OBzl) (3.6 g), a solution of 2.06 g DCC in 10 ml chloroform was added under ice cooling, and the mixture was stirred under ice cooling for one hour and then at room temperature overnight. Precipitated dicyclohexylurea was filtered off, the filtrate was concentrated under reduced pressure, and the residue was dissolved in 150 ml of ethyl acetate. This solution was washed with 2N-HCl, water, 4% aqueous solution of sodium bicarbonate, water and saturated aqueous solution of sodium chloride in that order, and dried over anhydrous sodium sulfate. After filtering off the drying agent, the filtrate was concentrated under reduced pressure. The residue was dissolved in 100 ml of 80% acetic acid, and the solution was subjected to catalytic reduction under a hydrogen gas stream at room temperature for four hours using palladium-carbon as catalyst. After filtering off the catalyst, the filtrate was concentrated under reduced pressure, and the residue was recrystallized from water, giving 1.8 g of D-alanyl-α-L-aspartyl-D-alanine isopropyl ester.

(B) N-Benzyloxycarbonyl-D-alanine N-hydroxysuccinimide ester

A solution of 10.3 g DCC in 20 ml tetrahydrofuran was added under ice cooling to a solution of 11.2 g N-benzyloxycarbonyl-D-alanine and 5.8 g N-hydroxysuccinimide in 150 ml tetrahydrofuran. The mixture was stirred under ice cooling for one hour and then at room temperature overnight. After precipitated dicyclohexylurea was filtered off, the filtrate was concentrated under reduced pressure, and the residue was recrystallized from ethanol, affording 12.8 g of N-benzyloxycarbonyl-D-alanine N-hydroxysuccinimide ester.

(C) N-Benzyloxycarbonyl-D-alanyl-α-L-aspartyl-D-alanine isopropyl ester

To a solution of 1.8 g α-L-aspartyl-D-alanine isopropyl ester and 0.6 g sodium bicarbonte in 50 ml water, was added with stirring a solution of 2.2 g N-benzyloxycarbonyl-D-alanine N-hydroxysuccinimide ester in 50 ml dioxane, and stirring was continued at room temperature for five hours. After the pH was adjusted to 2.5 with 6N-HCl, 150 ml ethyl acetate was added and the mixture was thoroughly agitated. The organic layer was collected, washed with water and then with saturated aqueous solution of sodium chloride, and dried over anhydrous sodium sulfate. After filtering off the drying agent, the filtrate was concentrated under reduced pressure, and the residue was purified by reprecipitation with ethyl acetate/hexane, giving 2.5 g of N-benzyloxycarbonyl-D-alanyl-α-L-aspartyl-D-alanine isopropyl ester.

(D) D-Alanyl-α-L-aspartyl-D-alanine isopropyl ester

N-Benzyloxycarbonyl-D-alanyl-α-L-aspartyl-D-alanine isopropyl ester (2.5 g) was dissolved in 100 ml of 80% aqueous acetic acid, and the solution was subjected to catalytic reduction in a hydrogen gas stream at room temperature for four hours using palladium/carbon as catalyst. After filtering off the catalyst, the filtrate was concentrated to dryness under reduced pressure, affording 1.6 g of white powder. M.p.: 219°–221° C.

EXAMPLE 17

D-Alanyl-α-L-aspartyl-L-phenylglycine methyl ester (A) α-L-Aspartyl-L-phenylglycine methyl ester This compound was prepared from 2.0 g L-phenylglycine methyl ester hydrochloride and 3.6 g Z-Asp(OBzl) in a manner similar to Example 16 (A). Yield: 2.0 g.

(B) D-Alanyl-α-L-aspartyl-L-phenylglycine methyl ester

This compound was prepared from 2.0 g α-L-aspartyl-L-phenylglycine methyl ester and 2.2 g N-benzyloxycarbonyl-D-alanine N-hydroxysuccinimide ester in a manner similar to Example 16 (C) and (D). Yield: 1.8 g, m.p.: 234°–234.5° C.

EXAMPLE 18

D-Alanyl-α-L-aspartyl-D-α-aminobutyric acid isopropyl ester (A) α-L-Aspartyl-D-α-aminobutyric acid isopropyl ester This compound was prepared from 1.8 g D-α-aminobutyric acid isopropyl ester hydrochloride and 3.6 g Z-Asp(OBzl) in a manner similar to Example 16 (A). Yield: 1.8 g.

(B) D-Alanyl-α-aspartyl-D-α-aminobutyric acid isopropyl ester

This compound was prepared from 1.9 g α-L-aspartyl-D-α-aminobutyric acid isopropyl ester and 2.2 g N-benzyloxycarbonyl-D-alanine N-hydroxysuccinimide ester in a manner similar to Example 16 (C) and (D). Yield: 1.8 g, m.p.: 229°–230° C.

EXAMPLE 19

D-Alanyl-L-α-aspartyl-D-serine isopropyl ester (A) α-L-Aspartyl-D-serine isopropyl ester This compound was prepared from 1.8 g D-serine isopropyl ester hydrochloride and 3.6 g Z-Asp(OBzl) in a manner similar to Example 16 (A). Yield: 1.9 g.

(B) D-Alanyl-α-L-aspartyl-D-serine isopropyl ester

This compound was prepared from 1.9 g α-L-aspartyl-D-serine isopropyl ester and 2.2 g N-benzyloxycarbonyl-D-alanine N-hydroxysuccinimide ester in a manner similar to Example 16 (C) and (D). Yield: 1.8 g, m.p.: 222.5°–234° C.

EXAMPLE 20

α-Aminoisobutyryl-α-L-aspartyl-L-phenylalanine methyl ester (A) α-L-Aspartyl-L-phenylalanine methyl ester This compound was prepared in a manner similar to Example 11 (A).

(B) N-t-Butoxycarbonyl-α-aminoisobutyric acid N-hydroxysuccinimide ester

A solution of 10.3 g DCC in 20 ml tetrahydrofuran was added under ice cooling to a solution of 10.2 g N-t-butoxycarbonyl-α-aminoisobutyric acid and 5.8 g N-hydroxysuccinimide in 150 ml tetrahydrofuran. The mixture was stirred under ice cooling for one hour and then at room temperature overnight.

After precipitated dicyclohexylurea was filtered off, the filtrate was concentrated under reduced pressure, and the residue was recrystallized from ethanol, affording 11.7 g of N-t-butoxycarbonyl-α-aminoisobutyric acid N-hydroxysuccinimide ester.

(C) N-t-Butoxycarbonyl-α-aminoisobutyryl-α-L-aspartyl-L-phenylalanine methyl ester To a solution of 1.9 g α-L-aspartyl-L-phenylalanine methylester and 0.6 g sodium bicarbonte in 50 ml water, was added with stirring a solution of 1.8 g N-t-butoxycarbonyl-α-aminoisobutyric acid N-hydroxysuccinimide ester in 50 ml dioxane, and stirring was continued at room temperature for five hours.

After the pH was adjusted to 2.5 with 6N-HCl, 150 ml ethyl acetate was added and the mixture was thoroughly agitated. The organic layer was collected, washed with water and then with saturated aqueous solution of sodium chloride, and dried over anhydrous sodium sulfate. After filtering off the drying agent, the filtrate was concentrated under reduced pressure, and the residue was purified by reprecipitation with ethyl acetate/hexane, giving 2.3 g of N-t-butoxycarbonyl-α-aminoisobutyryl-α-L-aspartyl-L-phenylalanine methyl ester.

(D) α-Aminoisobutyryl-α-L-aspartyl-L-phenylalanine methyl ester hydrochloride

N-t-Butoxycarbonyl-α-aminoisobutyryl-α-L-aspartyl-L-phenylalanine methyl ester (2.3 g) was dissolved under ice cooling in 4N-HCl/dioxane (20 ml), and the mixture was stirred for one hour. Ethyl ether (150 ml) was added, and the crystals which separated out were collected by filtration. Yield: 1.8 g.

(E) α-Aminoisobutyryl-α-L-aspartyl-L-phenylalanine methyl ester

A solution of 1.8 g α-aminoisobutyryl-α-L-aspartyl-L-phenylalanine methyl ester hydrochloride in 50 ml water was allowed to pass through a column (50 ml) packed with a weakly basic anion-exchange resin (Dow Chemical Co., "IRA-68"), and the resin was washed with 100 ml water. The washings were added to the effluent, and the combined solution was concentrated under reduced pressure, giving 1.4 g of white powder. M.p.: 168°-170° C.

EXAMPLE 21

α-Aminoisobutyryl-α-L-aspartyl-D-alanine isopropyl ester

This compound was prepared from 1.7 g D-alanine isopropyl ester hydrochloride, 3.6 g Z-Asp(OBzl) and 1.8 g N-t-butoxycarbonyl-α-aminoisobutyric acid N-hydroxysuccinimide ester in a manner similar to Example 20 (A), (C), (D) and (E). Yield: 1.2 g, m.p.: 176°-178° C.

EXAMPLE 22

α-Aminoisobutyryl α-L-aspartyl-L-phenylglycine methyl ester

This compound was prepared from 2.0 g L-phenylglycine methyl ester hydrochloride, 3.6 g Z-Asp(OBzl) and 1.8 g N-t-butoxycarbonyl-α-aminoisobutyric acid N-hydroxysuccinimide ester in a manner similar to Example 20 (A), (C), (D) and (E). Yield: 1.4 g, m.p.: 175°-177° C.

EXAMPLE 23

α-Aminoisobutyryl-α-L-aspartyl-D-serine ethyl ester

This compound was prepared from 1.7 g D-serine ethyl ester hydrochloride, 3.6 g Z-Asp(OBzl) and 1.8 g N-t-butoxycarbonyl-α-aminoisobutyric acid N-hydroxysuccinimide ester in a manner similar to Example 20 (A), (C), (D) and (E). Yield: 1.2 g, m.p.: 175°-178° C.

EXAMPLE 24

α-Aminoisobutyryl-α-L-aspartyl-D-aminobutyric acid isopropyl ester

This compound was prepared from 1.8 g D-aminobutyric acid isopropyl ester hydrochloride, 3.6 g Z-Asp(OBzl) and 1.8 g N-t-butoxycarbonyl-α-aminoisobutyric acid N-hydroxysuccinimide ester in a manner similar to Example 20 (A), (C), (D) and (E). Yield: 1.3 g, m.p.: 179°-180° C.

EXAMPLE 25

D-Alanyl-L-α-aspartyl-D-alanine n-propyl ester (A) α-L-Aspartyl-D-alanine n-propyl ester This compound was prepared from 1.8 g D-alanine n-propyl ester hydrochloride and 3.6 g Z-Asp(OBzl) in a manner similar to Example 16 (A). Yield: 1.9 g.

(B) D-Alanyl-α-L-aspartyl-D-alanine n-propyl ester:

This compound was prepared from 1.9 g α-L-aspartyl-D-alanine n-propyl ester and 2.2 g N-benzyloxycarbonyl-D-alanine N-hydroxysuccinimide ester in a manner similar to Example 16 (C) and (D). Yield: 1.7 g, m.p.: 223°-225° C.

What is claimed is:

1. A tripeptide represented by formula (I)

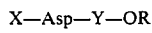

wherein
X stands for an amino acid residue which is a D or DL-isomer except when it is glycine, which is linked, at its carboxyl group, to the amino group of L-aspartic acid through peptide bonding and is selected from the group consisting of glycine, alanine, α-aminobutyric acid, serine, threonine, norvaline, asparagine, β-methyl aspartate, proline, and pipecolic acid;
Asp denotes an L-aspartic acid residue which is linked, at its amino group, to the amino acid residue X through peptide bonding and is connected, at its carboxyl group attached to the amino-substituted carbon atom, to the amino acid residue Y through peptide bonding;
Y stands for an amino acid residue which is a D, L or DL-isomer, which is linked, at its amino group, to Asp through peptide bonding and is concentrated, at its carboxyl group, to an alcohol ester bonding and is selected from the group consisting of alanine, phenylalanine, phenylglycine, serine, and α-aminobutyric acid, and salts thereof; and
OR represents an alkoxy residue linked, at its hydroxyl group, to the amino acid residue Y through ester bonding;
R denotes an alkyl group selected from the group consisting of methyl, ethyl, propyl, and isopropyl.

2. The compound as defined in claim 1 wherein X is alanine residue, Y is phenylalanine residue, R is methyl, and the amino acid residues X and Y are D-isomer and L-isomer, respectively.

3. The compound as defined in claim 1 wherein X is alanine residue, Y is alanine residue, R is isopropyl or n-propyl, and the amino acid residues X and Y are both D-isomers.

4. The compound as defined in claim 1 wherein X is proline residue, Y is phenylalanine residue, R is methyl, and the amino acid residues X and Y are D-isomer and L-isomer, respectively.

5. Sweetening agents containing a tripeptide according to claim 1, or a salt thereof as the effective ingredient.

6. A method for sweetening edible materials which comprises adding thereto an effective amount of a tripeptide according to claim 1 or a salt thereof.

* * * * *